United States Patent [19]

Damani et al.

[11] Patent Number: 5,447,725

[45] Date of Patent: * Sep. 5, 1995

[54] METHODS FOR AIDING PERIODONTAL TISSUE REGENERATION

[75] Inventors: Nalinkant C. Damani, Cincinnati; Douglas C. Mohl; Robert E. Singer, Jr., both of Fairfield, all of Ohio

[73] Assignee: The Procter & Gamble Company, Cincinnati, Ohio

[*] Notice: The portion of the term of this patent subsequent to Mar. 30, 2010 has been disclaimed.

[21] Appl. No.: 76,304

[22] Filed: Jun. 11, 1993

[51] Int. Cl.⁶ .................... A61K 9/06; A61K 31/65; A61K 31/74
[52] U.S. Cl. .................... 424/435; 424/426; 424/434; 424/486; 514/152; 514/772.3; 514/772.6; 514/900; 514/902; 514/944; 514/953
[58] Field of Search ............. 424/426, 434, 435, 486; 514/152, 772.3, 772.6, 900, 902, 944, 953

[56] References Cited

U.S. PATENT DOCUMENTS

| | | | |
|---|---|---|---|
| Re. 33,093 | 10/1989 | Schiraldi et al. | 424/676 |
| 2,976,251 | 3/1961 | Brokaw et al. | 252/316 |
| 3,498,957 | 3/1970 | Jacobson | 260/78.3 |
| 3,636,956 | 1/1972 | Schneider | 128/335.5 |
| 3,736,646 | 6/1973 | Schmitt et al. | 29/458 |
| 3,867,190 | 2/1975 | Schmitt et al. | 117/138.8 |
| 3,978,203 | 8/1976 | Wise | 424/22 |
| 4,017,615 | 4/1977 | Shastri et al. | 424/241 |
| 4,098,885 | 7/1978 | Curtis | 424/212 |
| 4,137,921 | 2/1979 | Okuzumi et al. | 128/335.5 |
| 4,175,326 | 11/1979 | Goodson | 433/80 |
| 4,191,747 | 3/1980 | Scheicher | 424/94 |
| 4,219,548 | 8/1980 | Reller | 424/234 |
| 4,226,848 | 10/1980 | Nagai et al. | 424/19 |
| 4,250,163 | 2/1981 | Nagai et al. | 424/14 |
| 4,328,204 | 5/1982 | Wasserman et al. | 424/19 |
| 4,443,430 | 4/1984 | Mattei et al. | 424/78 |
| 4,454,110 | 6/1984 | Caslavsk et al. | 424/54 |
| 4,474,750 | 10/1984 | Gaffar et al. | 424/49 |
| 4,568,535 | 2/1986 | Loesche | 424/19 |
| 4,568,536 | 2/1986 | Kronenthal et al. | 424/22 |
| 4,569,837 | 2/1986 | Suzuki et al. | 424/28 |
| 4,603,076 | 7/1986 | Bowditch et al. | 428/246 |
| 4,615,697 | 10/1986 | Robinson | 604/890 |
| 4,624,256 | 11/1986 | Messier et al. | 128/335.5 |
| 4,644,018 | 2/1987 | Bowditch et al. | 521/130 |
| 4,650,665 | 3/1987 | Kronenthal et al. | 424/435 |
| 4,652,441 | 3/1987 | Okada et al. | 424/19 |
| 4,670,252 | 6/1987 | Sampathkumar | 424/53 |
| 4,685,883 | 8/1987 | Jernberg | 438/215 |
| 4,692,328 | 9/1987 | Kitchell et al. | 424/78 |
| 4,699,823 | 10/1987 | Kellenberger et al. | 428/219 |
| 4,711,782 | 12/1987 | Okada et al. | 424/455 |
| 4,713,243 | 12/1987 | Schiraldi et al. | 424/151 |
| 4,725,628 | 2/1988 | Garvey et al. | 521/137 |
| 4,725,629 | 2/1988 | Garvey et al. | 521/137 |
| 4,731,391 | 3/1988 | Garvey | 521/137 |
| 4,764,377 | 9/1988 | Goodson | 424/435 |
| 4,769,414 | 9/1988 | Kightlinger et al. | 525/54.24 |
| 4,772,484 | 9/1988 | Kitchell et al. | 427/2 |
| 4,780,320 | 10/1988 | Baker | 424/493 |

(List continued on next page.)

FOREIGN PATENT DOCUMENTS

| | | | |
|---|---|---|---|
| 0140766 | 6/1985 | European Pat. Off. | A61K 6/02 |
| 0130690 | 9/1985 | European Pat. Off. | A61K 9/70 |
| 0241179 | 10/1987 | European Pat. Off. | A61K 9/70 |
| 0275550 | 7/1988 | European Pat. Off. | A61K 9/70 |
| 3635679A | 5/1988 | Germany | A62L 17/00 |
| 63-79817 | 4/1988 | Japan | A61K 9/06 |
| 63-287719 | 11/1988 | Japan | A61K 9/06 |

Primary Examiner—Thurman K. Page
Assistant Examiner—Carlos Azpuru
Attorney, Agent, or Firm—Kim William Zerby; Douglas C. Mohl; Jacobus C. Rasser

[57] ABSTRACT

Methods for aiding periodontal tissue regeneration with compositions containing bioresorbable polymers, leachable solvents, and bioavailable drug actives. The compositions useful for these methods are characterized by becoming harder upon contact with the periodontal tissue such that the composition is effective for aiding tissue regeneration and by releasing a therapeutically-effective amount of drug active agent.

14 Claims, No Drawings

U.S. PATENT DOCUMENTS

| | | | |
|---|---|---|---|
| 4,788,062 | 11/1988 | Gale et al. | 424/449 |
| 4,795,436 | 1/1989 | Robinson | 424/422 |
| 4,810,775 | 3/1989 | Bendix et al. | 528/480 |
| 4,818,534 | 4/1989 | Levy | 424/404 |
| 4,839,215 | 6/1989 | Starling et al. | 428/131 |
| 4,863,970 | 9/1989 | Patel et al. | 514/784 |
| 4,892,736 | 1/1990 | Goodson | 424/435 |
| 4,900,552 | 2/1990 | Sanvordeker et al. | 424/422 |
| 4,900,554 | 2/1990 | Yanagibashi et al. | 424/448 |
| 4,920,203 | 4/1990 | Tang et al. | 525/409 |
| 4,933,182 | 6/1990 | Higashi et al. | 424/435 |
| 4,969,884 | 11/1990 | Yum | 604/892.1 |
| 5,030,216 | 7/1991 | Theeuwes et al. | 604/892.1 |
| 5,061,281 | 10/1991 | Mares et al. | 623/11 |
| 5,084,267 | 1/1992 | Damani | 424/426 |
| 5,143,934 | 9/1992 | Lading et al. | 514/396 |
| 5,198,220 | 3/1993 | Damani | 424/426 |
| 5,200,195 | 4/1993 | Dong et al. | 424/473 |
| 5,242,910 | 9/1993 | Damani | 514/152 |

…

METHODS FOR AIDING PERIODONTAL TISSUE REGENERATION

BACKGROUND OF THE INVENTION

The present invention relates to methods for aiding periodontal tissue regeneration with compositions containing bioresorbable polymers, leachable solvents, and bioavailable drug actives.

Periodontal disease is a major concern in dentistry. Periodontal tissues are often lost with the progression of periodontal disease. Loss of periodontal tissue compromises the prognosis for retention of teeth in the dental arch, often creates an unhealthy environment in the mouth and may be unsightly.

Various methods have been used to facilitate regeneration of lost or diseased periodontal tissue. Periodontal barriers are sometimes surgically implanted adjacent the root of the tooth, or wherever tissue loss has occurred, by periodontal surgery to aid and guide tissue regeneration along the tooth surface where periodontal tissue regeneration is desired. Presently, these barriers are comprised of materials such as polytetrafluroethylene (PTFE) which is biocompatible and non-resorbable. The barriers are typically removed after 4-6 weeks by a surgical re-entry procedure. Resorbable barriers are also being investigated for potential use in periodontal guided tissue regeneration. For example, crosslinked collagen is being studied in this regard.

It is often difficult to obtain the periodontal tissue growth desired since the regeneration of periodontal tissue is variable. Moreover, surgical implantation of barriers can be associated with infection and inflammation. Infection and excessive inflammation can adversely effect tissue regeneration with the use of periodontal barriers for guiding healing. Therefore it would be beneficial to be able to treat the tissue regeneration site with antibiotics, anti-inflammatories, or other appropriate chemotherapeutic agents as required to facilitate periodontal tissue regeneration. Also, the use of carrier agents in conjunction with appropriate chemotherapeutic agents to enhance cellular uptake of the chemotherapeutic agents would be helpful in the regeneration of periodontal tissue.

A potential problem envisioned with the use of chemotherapeutic agents in conjunction with periodontal barriers is how to control and regulate the delivery and uptake of such agents to the tissue regeneration site over an extended predetermined period of time so as to obtain the desired periodontal tissue growth.

The use of microparticles containing chemotherapeutic agents, and their use as periodontal barriers and in methods for aiding periodontal tissue regeneration, are known being described, for example, in U.S. Pat. No. 4,685,883, issued Aug. 11, 1987 and U.S. Pat. No. 5,059,123, issued Oct. 22, 1991, both to Jernberg, both incorporated herein by reference in their entirety. In the former patent, the microcapsules are said to be deposited in the periodontal pocket or attached to a root surface of the tooth for treatment of the periodontal disease itself, and not incorporated into a barrier for aiding or guiding periodontal tissue regeneration. The latter patent uses periodontal barriers made of body compatible materials (said to include resorbable and nonresorbable materials and which may also preferably incorporate microencapsulated chemotherapeutic agents) to aid periodontal tissue regeneration, which barriers are taught to be surgically implanted by conventional techniques and sutured in place by use of body compatible sutures.

In spite of such research, there continues to be a need for improved compositions and methods for aiding periodontal tissue regeneration. It is therefore an object of the present invention to provide methods for aiding periodontal tissue regeneration which are easy to administer, comfortable for the patient, and/or avoid the need for suturing and/or subsequent surgery to remove the compositions. An additional object is to provide bioresorbable compositions effective for periodontal tissue regeneration which provide sustained release of drug actives while supporting regeneration of periodontal tissue. An object is also to provide methods for aiding periodontal tissue regeneration which eliminate the need to suture the compositions at the treatment site.

These and other objects of the present invention will become readily apparent from the detailed description which follows.

All percentages and ratios used herein are by weight unless otherwise specified.

SUMMARY OF THE INVENTION

The present invention relates to methods for aiding periodontal tissue regeneration in a human or lower animal. Said method comprises placing at the site in need of periodontal tissue regeneration in a human or lower animal a composition comprising a bioresorbable polymer, leachable solvent, and bioavailable drug active agents, wherein said composition is further characterized by becoming harder upon contact with the periodontal tissue such that the composition is effective for aiding tissue regeneration, and by releasing a therapeutically-effective amount of drug active agent.

DETAILED DESCRIPTION OF THE INVENTION

The method of the present invention relates to aiding periodontal tissue regeneration. These methods comprise placing at the periodontal site in a human or lower animal in need of periodontal tissue regeneration a composition comprising a bioresorbable polymer, leachable solvent, and bioavailable drug active agent. Said composition is further characterized by becoming harder upon contact with the periodontal tissue such that the composition is effective for aiding tissue regeneration and by releasing a therapeutically-effective amount of drug active agent.

The specific location of the placement of the composition, and the method of placement, depend on the periodontal site in need of tissue regeneration and the form of the composition prior to placement at the site. For example, compositions useful for the method of the present invention in the form of shaped devices such as thin compositions become harder to provide effective support for the tissue regeneration. With regard to the specific placement site of the composition, such determinations are readily made by the attending dentist or physician in light of the specific periodontal tissue loss to be corrected. The specific configuration of the composition and the site of its placement will depend on such things as the anatomy of the tooth root(s), the periodontal defect, and the growth that is desired, which are within the knowledge of the attending professional.

The fluid or viscous gel compositions useful for the methods of the present development may also be used without surgically removing the entire gum tissue. A syringable composition of the present invention is placed in the cavity around the tooth, against the tooth surface. If necessary, one or more incisions at the site of the disease are made to remove the infected tissue only, but keeping intact the attached ligaments from the tissue to the tooth surface. If any incision is made, they are closed or sutured using a conventional technique.

The syringable compositions of the present invention becomes near solid encasing the tooth surface. One or more active agents present in the compositions slowly release from the polymeric matrix due to erosion of the matrix and some diffusion through the matrix. In practice, the bioerodible copolymers useful in the present invention provide a support for the growth of the tissue, while one or more active agents help heal the tissue at a rapid rate.

Since the components of the present invention are bioerodible, they dissipate with time in about 1 to 12 weeks, and it is not necessary to remove the compositions.

The essential as well as optional components of the compositions/devices useful for the methods of this invention are described below.

Bioresorbable Polymers

The term "bioresorbable polymer", as used herein, means those polymer materials which are safe for use in the oral cavity of a human or lower animal, which are solubilized or plasticized by inclusion of leachable solvents and thereby harden upon placement of compositions containing the polymer in the periodontal tissue, and which slowly degrade in the periodontal tissue. Such polymers are known, including for example polymers and copolymers such as polylactic acid ("PLA"), polyglycolic acid ("PLG"), poly lactyl-co-glycolic acid ("PLGA"), polyaminoacids such as polyaspartame, chitosan, collagen, polyalbumin, gelatin and hydrolyzed animal protein, xanthan and other water soluble gums, polyanhydride, and poly orthoesters. Preferred are polymers and copolymers of polylactic acid ("PLA"), polyglycolic acid ("PLG"), and poly lactyl-co-glycolic acid ("PLGA").

Most preferred bioresorbable polymer useful for the present invention are the copolymers containing mixtures of lactide and glycolide monomers. Lactide monomeric species preferably comprise from about 15% to about 85%, most preferably from about 35% to about 65% of the polymers, while glycolide monomeric species comprise from about 15% to about 85% of the polymer, preferably from about 35% to about 65% on a molar basis. The molecular weight of the copolymer typically lies in the range of from about 1000 to about 120,000 (number average). These polymers are described in detail in U.S. Pat. No. 4,443,430, Apr. 17, 1984, to Mattei incorporated herein by reference in its entirety.

A feature of fluid gel or paste-like compositions containing such copolymers is their transformation into near solid phase in the presence of aqueous fluid such as water, aqueous buffers, serum, crevicular fluid, or other body fluid. For example, when a sample of such a gel is placed into a tube containing water or human serum, the composition becomes nearly solid in the receptor phase. This is believed to be due to insolubility of the poly(lactyl-co-glycolide) copolymer in water, and related aqueous solvents such as may be present in crevicular fluid. Thus, even though such fluid compositions can be used advantageously when desired from a syringe-like apparatus, they still offer the uncompromised advantages of solid devices at the treatment sites. Further, since such polymeric materials do undergo slow degradation via hydrolysis, the drug continues to release in a sustained manner from such compositions and the composition does not need to be surgically removed following tissue regeneration.

The polymer generally comprises from about 1% to about 90%, preferably from about 10% to about 70%, of the compositions/devices useful for the methods of the present invention. Generally, for the most preferred copolymers containing lactide and glycolide, less polymer is necessary as the amount of lactide goes up.

Leachable Solvent

The term "leachable solvent", as used herein, means a material or combination of materials which solubilize and/or plasticize the bioresorbable polymers and which are soluble in the periodontal tissue, body fluid or pocket fluid, to the extent that the solvent material(s) leaches from the polymer following placement of the polymer composition in the periodontal tissue. Leachable solvents include, for example, propylene carbonate, glyceryl triacetate ("triacetin"), triethyl citrate ("Citroflex"), and mixtures thereof.

One preferred leachable solvent material is propylene carbonate. This is a material of commerce and is used in the present compositions/devices at a level of from about 0.1% to about 90%, preferably from about 1% to about 70%, most preferably from about 3% to about 50%. The higher levels of propylene carbonate, such as from about 25% to about 90%, are used when it is desired that the compositions be in gel or liquid form rather than in solid form.

Another preferred leachable solvent material is triacetin. Triacetin, known chemically as 1,2,3-propanetriol triacetate or glyceryl triacetate, is a commercially available material and is prepared by the acetylation of glycerol. Triacetin is used in the present compositions/devices at a level of from about 1% to about 90%, preferably from about 1% to about 70%, most preferably from about 3% to about 50%. The higher levels of triacetin, such as from about 20% to about 90%, are used when it is desired that the compositions be in gel or liquid form rather than in solid form. Gel form of the present invention compositions is most preferred, and typically comprise from about 25% to about 50% triacetin.

Finally, to adjust the viscosity of the final composition and/or to vary the rate of solvent leaching, mixtures of triethyl citrate, propylene carbonate and/or triacetin may be used, alone or in combination with other materials.

Drug Active

The drugs useful for use in the present compositions/devices are varied and many and include any agent which provides treatment or prevention management of diseases of the oral cavity when placed in the periodontal tissue. Some therapeutic agents, which are amenable to delivery by this means and are potentially of value for periodontal therapy, include (but are not limited to) antibacterial agents such as iodine, sulfonamides, mercurials, bisbiguanides, or phenolics; antibiotics such as tetracycline, neomycin, kanamycin, metronidazole, or clindamycin; anti-inflammatory agents such as aspirin, naproxen, ibuprofen, flurbiprofen, indomethacin, eugenol, or hydrocortisone; immune-suppressive or stimulatory agents such as methotrexate or levamasole; dentinal desensitizing agents such as strontium chloride or sodium fluoride; odor masking agents such as peppermint oil or chlorphyll; immune reagents such as immunoglobulin or antigens; local anesthetic agents such as lidocaine or benzocaine; nutritional agents such as amino acids, essential fats, and vitamin C; antioxidants such as alphatocopherol and butylated hydroxy toluene; lipopolysaccharide complexing agents such as polymyxin; peroxides such as urea peroxide; growth factors such as insulin, PDGf (platelet derived growth factors), BMP (bone morphogenic proteins), PDLgf (periodontal ligament chemotactic factor), $TGF_B$ (tissue growth factor beta), insulin-like growth factor 1; or clot stabilizing factors, such as fibrin and factor IX complex. It is recognized that in certain forms of therapy, combinations of these agents in the same delivery system may be useful in order to obtain an optimal effect. Thus, for example, an antibacterial and an anti-inflammatory agent may be combined in a single delivery system to provide combined effectiveness.

The drug active is used at a level of from about 0.1% to about 90%, preferably from about 0.1% to about 75%, most preferably from about 1% to about 50% of the compositions/devices. The compositions/devices, for example, are designed to release drug to provide steady state number average concentrations of from about 10 µg to about 2000 µg, preferably from about 25 µg to about 1500 µg, most preferably from about 50 µg to about 500 µg per milliliter of the body fluid of the treated periodontal site.

The steady state release rates can be altered by varying component ratios of the compositions. The steady state conditions are preferably used since initial bursts are accounted for as well as delays in release. For example, in the case of a ten (10) day therapy, steady state is generally reached in about one to three days.

Optional Components

In addition to the drug active, the compositions/devices of the present invention may include a variety of optional components. Such components include, but are not limited to, surfactants, flavoring agents, viscosity controlling agents, complexing agents, antioxidants, other polymers such as carboxymethyl cellulose, gums such as guar gum, waxes/oils such as castor wax, castor oil, glycerol, dibutyl phthalate and di(2-ethylhexyl) phthalate, calcium salts (e.g., hydroxyapatite; calcium phosphate), coloring agents, as well as many others. A preferred optional component is collagen which may assist in the tissue regeneration by its localized presence in the site in which the composition is placed. If used, these optional components comprise from about 0.1% to about 20%, preferably from about 0.5% to about 5% of the total composition/device.

The following Examples further describe and demonstrate embodiments within the scope of the present invention. The Examples are given solely for the purpose of illustration and are not to be construed as limitations of the present invention as many variations thereof are possible without departing from its spirit and scope.

EXAMPLES 1-5

The following are exemplary of syringable compositions useful for the methods of the present invention:

| Example: | Components: | Weight % |
|---|---|---|
| 1. | Doxycycline hyclate | 15.0 |
| | Triacetin | 50.0 |
| | PLGA co-polymer(s) | 35.0 |
| 2. | Metronidazole | 10.0 |
| | Fibrinogen (purified) | 5.0 |
| | PLGA co-polymer(s) | 30.0 |
| | Triethyl citrate | 55.0 |
| 3. | Minocycline HCl | 25.0 |
| | Growth Factor: $TGF_B$ | 1.0 |
| | Fibrinogen (purified) | 4.0 |
| | PLGA co-polymer(s) | 30.0 |
| | Propylene carbonate | 40.0 |
| 4. | Ciprofloxacin HCl | 10.0 |
| | Factor IX Complex, Heat Treated | 5.0 |
| | PLGA co-polymer(s) | 35.0 |
| | Propylene carbonate | 50.0 |
| 5. | Tetracycline HCl | 25.0 |
| | Naproxen | 10.0 |
| | Collagen, Soluble | 5.0 |
| | PLGA co-polymer(s) | 20.0 |
| | Propylene carbonate | 40.0 |

The gum tissue of a periodontally involved tooth is vertically slit from the margin down toward the root of the tooth without further damaging the remaining attachment ligaments. One to six such slits are made around the circumference of the tooth. A paste-like composition according to any of Examples 1-5 containing active agent is placed through one or more of these slits via semi-flexible catheter from a syringe-like apparatus adjacent to the tooth surface. The slits are closed by using either sutures or a surgical adhesive.

The paste-like compositions transform by hardening at the placement site into a flexible membrane adjacent to the tooth surface. This film acts as a support and guides growth of new periodontal membrane, while slowly releasing active agent. In about 2-8 weeks following the product placement, the health of the tissue improves toward normal. The polymers in the present invention compositions slowly degrade and dissipate eliminating any need for a second surgical intervention to remove the composition.

EXAMPLES 6-7

The following are pre-formed membranes which may be used when desired for larger cavities to be treated according to the present invention:

| Example: | Components: | Weight % |
|---|---|---|
| 6. | Tetracycline HCl | 45.0 |
| | Triacetin | 6.0 |
| | PLGA co-polymer(s) | 49.0 |
| 7. | Minocycline HCl | 25.0 |
| | Collagen, soluble | 8.0 |
| | PLGA co-polymer(s) | 63.0 |
| | Propylene carbonate | 4.0 |

A flexible, semi-rigid preformed membrane according to either of Examples 6 or 7 is cut in size and shape to fit the circumference of a periodontally involved tooth. Although a surgical slit procedure as described hereinbefore for Examples 1-5 may be employed, it is easier to use a surgical flap procedure to place a preformed membrane adjacent to the root surface, followed by either suturing the gum tissue or closing with a surgical adhesive. The membrane hardens upon placement adjacent to the root surface. The medicament contained in the membrane is slowly released over a 1-8 week period, providing activity of the drug while the bioresorbable membrane itself acts as support to guide the formation of periodontal membrane.

What is claimed:

1. A method for aiding periodontal tissue regeneration in a human or lower animal, said method comprises placing at the site in need of periodontal tissue regeneration in a human or lower animal a composition comprising a bioresorbable polymer, leachable solvent, and bioavailable drug active agents, wherein said composition is further characterized by becoming harder upon contact with the periodontal tissue such that the composition is effective for aiding tissue regeneration, and by releasing a therapeutically-effective amount of drug active agent.

2. The method for aiding periodontal tissue regeneration according to claim 1 wherein the bioresorbable polymer is selected from the group consisting of polylactic acid, polyglycolic acid, poly lactyl-co-glycolic acid, polyaminoacids, chitosan, collagen, polyalbumin, gelatin, hydrolyzed animal protein, water soluble gums, polyanhydride, and poly orthoesters.

3. The method for aiding periodontal tissue regeneration according to claim 1 wherein the leachable solvent is selected from the group consisting of propylene carbonate, glyceryl triacetate, triethyl citrate, and mixtures thereof.

4. The method for aiding periodontal tissue regeneration according to claim 1 wherein the bioavailable drug active is selected from the group consisting of antibacterial agents, antibiotics, anti-inflammatory agents, stimulatory agents, dentinal desensitizing agents, odor masking agents, immune reagents, local anesthetic agents, nutritional agents, antioxidants, lipopolysaccharide complexing agents, peroxides, growth factors, clot stabilizing factors, and mixtures thereof.

5. The method for aiding periodontal tissue regeneration according to claim 4 wherein the bioavailable drug active is selected from the group consisting of iodine, sulfonamides, mercurials, bisbiguanides, phenolics, tetracycline, neomycin, kanamycin, metronidazole, clindamycin, aspirin, naproxen, ibuprofen, flurbiprofen, indomethacin, eugenol, hydrocortisone, methotrexate, levamasole, strontium chloride, sodium fluoride, peppermint oil, chlorphyll, immunoglobulin, antigens, lidocaine, benzocaine, amino acids, essential fats, vitamin C, alphatocopherol, butylated hydroxy toluene, polymyxin, urea peroxide, insulin, platelet derived growth factors, bone morphogenic proteins, periodontal ligament chemotactic factor, tissue growth factor beta, IGF-1, fibrin, factor IX complex, and mixtures thereof.

6. The method for aiding periodontal tissue regeneration according to claim 4 wherein the bioresorbable polymer is selected from the group consisting of polylactic acid, polyglycolic acid, and poly lactyl-co-glycolic acid.

7. A method for aiding periodontal tissue regeneration in a human or lower animal, said method comprises placing at the site in need of periodontal tissue regeneration in a human or lower animal a composition comprising:

(a) a bioresorbable polymer selected from the group consisting of polylactic acid, polyglycolic acid, and poly lactyl-co-glycolic acid;

(b) leachable solvent selected from the group consisting of propylene carbonate, glyceryl triacetate, triethyl citrate, and mixtures thereof, and (c) bioavailable drug active agents, and wherein said composition is further characterized by becoming harder upon contact with the periodontal tissue such that the composition is effective for aiding tissue regeneration, and by releasing a therapeutically-effective amount of drug active agent.

8. The method for aiding periodontal tissue regeneration according to claim 7 wherein the bioavailable drug active is selected from the group consisting of antibacterial agents, antibiotics, anti-inflammatory agents, stimulatory agents, dentinal desensitizing agents, odor masking agents, immune reagents, local anesthetic agents, nutritional agents, antioxidants, lipopolysaccharide complexing agents, peroxides, growth factors, clot stabilizing factors, and mixtures thereof.

9. The method for aiding periodontal tissue regeneration according to claim 8 wherein the bioavailable drug active is selected from the group consisting of iodine, sulfonamides, mercurials, bisbiguanides, phenolics, tetracycline, neomycin, kanamycin, metronidazole, clindamycin, aspirin, naproxen, ibuprofen, flurbiprofen, indomethacin, eugenol, hydrocortisone, methotrexate, levamasole, strontium chloride, sodium fluoride, peppermint oil, chlorphyll, immunoglobulin, antigens, lidocaine, benzocaine, amino acids, essential fats, vitamin C, alphatocopherol, butylated hydroxy toluene, polymyxin, urea peroxide, insulin, platelet derived growth factors, bone morphogenic proteins, periodontal ligament chemotactic factor, tissue growth factor beta, IGF-1, fibrin, factor IX complex, and mixtures thereof.

10. The method for aiding periodontal tissue regeneration according to claim 7 wherein the method comprises placing by syringing at the site in need of periodontal tissue regeneration a composition in a form of a fluid or viscous gel capable of being syringed adjacent to a tooth surface.

11. A method for aiding periodontal tissue regeneration in a human or lower animal, said method comprises placing at the site in need of periodontal tissue regeneration in a human or lower animal a composition comprising:

(a) from about 1% to about 90% bioresorbable polymer selected from poly lactyl-co-glycolic acid;

(b) from about 0.1% to about 90% leachable solvent selected from the group consisting of propylene carbonate, glyceryl triacetate, triethyl citrate, and mixtures thereof, and (c) from about 0.1% to about 90% bioavailable drug active agents selected from the group consisting of antibacterial agents, antibiotics, anti-inflammatory agents, immune-suppressive agents, stimulatory agents, dentinal desensitizing agents, odor masking agents, immune reagents, local anesthetic agents, nutritional agents, antioxidants, lipopolysaccharide complexing agents, peroxides, growth factors, clot stabilizing factors, and mixtures thereof;

and wherein said composition is further characterized by becoming harder upon contact with the periodontal tissue such that the composition is effective for aiding tissue regeneration, and by releasing a therapeutically-effective amount of drug active agent.

12. The method for aiding periodontal tissue regeneration according to claim 11 wherein the poly lactyl-co-glycolic acid bioresorbable polymers comprise from about 15% to about 85% lactide monomeric species and from about 15% to about 85% glycolide monomeric species, on a molar basis; and wherein further the number average molecular weight of the copolymer lies in the range of from about 1000 to about 120,000.

13. The method for aiding periodontal tissue regeneration according to claim 12 wherein the bioavailable drug active is selected from the group consisting of iodine, sulfonamides, mercurials, bisbiguanides, phenolics, tetracycline, neomycin, kanamycin, metronidazole, clindamycin, aspirin, naproxen, ibuprofen, flurbiprofen, indomethacin, eugenol, hydrocortisone, methotrexate, levamasole, strontium chloride, sodium fluoride, peppermint oil, chlorphyll, immunoglobulin, antigens, lidocaine, benzocaine, amino acids, essential fats, vitamin C, alphatocopherol, butylated hydroxy toluene, polymyxin, urea peroxide, insulin, platelet derived growth factors, bone morphogenic proteins, periodontal ligament chemotactic factor, tissue growth factor beta, IGF-1, fibrin, factor IX complex, and mixtures thereof.

14. The method for aiding periodontal tissue regeneration according to claim 11 wherein the method comprises placing by syringing at the site in need of periodontal tissue regeneration a composition in a form of a fluid or viscous gel capable of being syringed adjacent to a tooth surface.

* * * * *